US006451758B1

(12) United States Patent
Markert et al.

(10) Patent No.: US 6,451,758 B1
(45) Date of Patent: Sep. 17, 2002

(54) ALDEHYDE MIXTURES, COMPOSITIONS CONTAINING THE SAME AND METHODS OF PROVIDING FRAGRANCE USING THE SAME

(75) Inventors: Thomas Markert, Monheim (DE); Theo Ten Pierik, Le Venlo (NL)

(73) Assignee: Cognis Deutschland GmbH, Dusseldorf (DE)

( * ) Notice: Subject to any disclaimer, the term of this patent is extended or adjusted under 35 U.S.C. 154(b) by 0 days.

(21) Appl. No.: 09/674,941

(22) PCT Filed: Apr. 29, 1999

(86) PCT No.: PCT/EP99/02902

§ 371 (c)(1),
(2), (4) Date: Jan. 12, 2001

(87) PCT Pub. No.: WO99/58629

PCT Pub. Date: Nov. 18, 1999

(30) Foreign Application Priority Data

May 8, 1998 (DE) ........................................ 198 20 657

(51) Int. Cl.[7] .................................................. A61K 7/46

(52) U.S. Cl. ............................... 512/27; 512/8; 512/25; 512/26

(58) Field of Search ................................ 512/8, 25, 26, 512/27

(56) References Cited

U.S. PATENT DOCUMENTS

| | | | | | |
|---|---|---|---|---|---|
| 4,283,561 | A | * | 8/1981 | Hagen et al. | 568/446 |
| 4,578,277 | A | * | 3/1986 | Morris et al. | 426/538 |
| 5,068,363 | A | | 11/1991 | Narula et al. | |

FOREIGN PATENT DOCUMENTS

| | | | |
|---|---|---|---|
| DE | 29 21 619 | A1 | 12/1980 |
| GB | 2 054 557 | * | 2/1981 |

* cited by examiner

*Primary Examiner*—Jill Warden
*Assistant Examiner*—Monique T. Cole
(74) *Attorney, Agent, or Firm*—John E. Drach; Aaron R. Ettelman

(57) ABSTRACT

Odoriferous compounds containing from 70 to 90% by weight of 2-methylene-3-(4-methlycyclohex-3-enyl)-butanal and from 10 to 30% by weight of limonene aldehyde, are described. The fragrance providing capabilities of the compounds are described in methods for their use, and perfumed compositions containing such compounds are also described.

14 Claims, No Drawings

ALDEHYDE MIXTURES, COMPOSITIONS CONTAINING THE SAME AND METHODS OF PROVIDING FRAGRANCE USING THE SAME

FIELD OF THE INVENTION

This invention relates to special perfume compositions containing 90 to 70% by weight of 2-methylene-3-(4-methylcyclohex-3-enyl)-butanal and 10 to 30% by weight of limonene aldehyde.

PRIOR ART

Limonene, for which the rational IUPAC name is 1-methyl4-isopropenyl cyclohex-1-ene, is a known natural substance. The structural formula of limonene (3) is shown below:

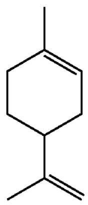

limonene (3).

It is known from DE 29 21 619 C3 that limonene can readily be converted into 3-(4-methylcyclohex-3-enyl)-butanal by hydroformylation. The hydroformylation is a reaction known to the expert which was discovered by Roelen in 1938. In this reaction, alkenes are converted into aldehydes with carbon monoxide and hydrogen. The reaction is also known as oxosynthesis.

The structural formula of 3-(4-methylcyclohex-3-enyl)-butanal, also referred to hereinafter as limonene aldehyde (2), is shown below:

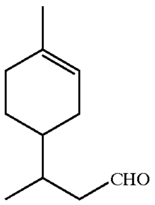

limonene aldehyde (2).

Now, according to DE 29 21 619 C3, limonene aldehyde can be converted by methylenation with formaldehyde into 2-methylene-3-(4-methylcyclohex-3-enyl)-butanal (1) which has the following structural formula:

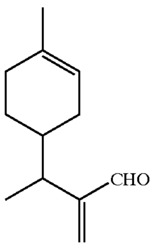

2-methylene-3-(4-methylcyclohex-3-enyl)-butanal (1).

According to the above-cited DE 29 21 619 C3, 2-methylene-3-(4-methylcyclohex-3-enyl)-butanal (1) may be used as a perfume. However, the document in question does not mention the properties of special mixtures of (1) with other olfactorily active compounds.

Judging by demand, many natural perfumes are available in totally inadequate quantities. Accordingly, it is clear that there is a constant demand in the perfume industry for new perfumes with interesting perfume notes in order to extend the range of naturally available perfumes and to be able to make the necessary adaptations to changing fashion trends and to satisfy the continuously increasing demand for odor enhancers for products of everyday use, such as cosmetics and cleaning products.

In addition, there is generally a constant need for synthetic perfumes which can be favorably produced in a consistent quality and which have desirable olfactory properties, i.e. pleasant, near-natural and qualitatively new odor profiles of adequate intensity, and which are capable of advantageously influencing the fragrance of cosmetic and consumer products. In other words, there is a constant need for compounds which have characteristic new odor profiles coupled with high staying power, intensity of odor and emanative power.

DESCRIPTION OF THE INVENTION

It has now surprisingly been found that special perfume compositions containing 90 to 70% by weight of 2-methylene-3-(4-methylcyclohex-3-enyl)-butanal (1) and 10 to 30% by weight of limonene aldehyde (2) are distinguished by extremely interesting perfume notes with fine nuances. The odor profiles of the perfume compositions according to the invention are different in quality, original and novel in relation to the individual components (1) and (2).

The present invention relates to perfume compositions containing 90 to 70% by weight of 2-methylene-3-(4-methylcyclohexen-3-enyl)-butanal (1) and 10 to 30% by weight of limonene aldehyde (2).

In one preferred embodiment, the perfume compositions according to the invention contain at most 5% by weight of other olfactorily active components besides the compulsory components (1) and (2) mentioned.

The present invention also relates to the use of aldehyde mixtures as perfumes, the aldehyde mixtures being mixtures containing 90 to 70% by weight of 2-methylene-3-(4-methylcyclohexen-3-enyl)-butanal (1) and 10 to 30% by weight of limonene aldehyde (2).

The odor profile of the perfume compositions according to the invention is original and novel. In perfume compositions, they enhance harmony and emanation and also staying power, the particular dosage being adapted to the perfume note required taking the other constituents of the composition into account.

By virtue of their odor profiles, the perfume compositions according to the invention are also particularly suitable for modifying and enhancing known compositions. Particular emphasis is placed above all on their ability to contribute towards the refinement of compositions.

Also remarkable is the way in which the perfume compositions according to the invention round off and harmonize the perfume notes of a broad range of known preparations without unpleasantly dominating them in any way.

The quantities in which the perfume compositions according to the invention are used in perfume preparations are between 0.001 and 70% by weight, based on the preparation as a whole. The perfume compositions according to the invention and corresponding preparations may be used both for perfuming cosmetic formulations, such as lotions, creams, shampoos, soaps, salves, powders, aerosols, toothpastes, mouthwashes, deodorants, and in extract perfumery. They may also be used for perfuming technical products and detergents and cleaning compositions, fabric softeners, textile treatment compositions and tobacco. For perfuming these various products, the preparations are added to them in an olfactorily effective quantity, more particularly in a concentration of 0.05 to 2% by weight, based on the product as a whole. However, these values are not intended to represent limits because the experienced perfumist can still obtain effects with lower concentrations or can build up new complexes with even higher concentrations.

The following Examples are intended to illustrate the invention without limiting it in any way.

EXAMPLES

1. Mixture of 80% (1) and 20% (2)

A perfume composition according to the invention was prepared by mixing 80% by weight, based on the composition as a whole, of 2-methylene-3-(4-methylcyclohex-3-enyl)-butanal (1) and 20% by weight, again based on the composition as a whole, of limonene aldehyde (2).

2. Perfume Test and Evaluation

Preparations P-1, P-2 and P-3 identified in Table 1 below were produced. Preparation P-1 (a Muguet preparation) is intended for comparison, preparation P-2 corresponds to the invention and preparation P-3 is another comparison preparation. In Table 1, the figures in the columns headed P-1 to P-3 represent parts by weight. So far as the components listed in column 1 are concerned, the various manufacturers are identified as follows:

* Henkel KGaA a) PFW (Perfume Flavours Worldwide)

b) Givaudan c) Charabot d) Hüls AG e) Firmenich

International Flavours and Fragrances.

Preparation P-2 has a distinctly fresher green citrus note than P-1, imparting a pleasant emanation and good diffusivity to the aldehydically flowery background and the harmonically tied-in wood base. By contrast, although preparation P-3 effectively emanates a fresh citrus note, the harmony from the balsamic background is seriously impaired and disturbed by an isolated vanilla note.

TABLE 1

| Component | P-1 | P-2 | P-3 |
|---|---|---|---|
| Aldehyde 11-11* | 1 | 1 | 1 |
| Herbavert* | 1 | 1 | 1 |
| Muguet aldehyde (e) | 1 | 1 | 1 |
| Ambroxan* | 1 | 1 | 1 |
| Indole | 2 | 2 | 2 |
| Boisambrene forte* | 4 | 4 | 4 |
| Sandelice* | 5 | 5 | 5 |
| Floramat* | 5 | 5 | 5 |
| Ylang, synthetic | 10 | 10 | 10 |
| Dihydroisojasmonate (a) | 20 | 20 | 20 |
| Cedrenyl acetate | 25 | 25 | 25 |
| Benzyl acetate | 30 | 30 | 30 |
| Linalool | 40 | 40 | 40 |
| Cinammic alcohol | 40 | 40 | 40 |
| Troenan* | 50 | 50 | 50 |
| Hexyl cinnamaldehyde, alpha | 100 | 100 | 100 |
| Lilial (b) | 140 | 140 | 140 |

TABLE 1-continued

| Component | P-1 | P-2 | P-3 |
|---|---|---|---|
| Rose (c) | 200 | 200 | 200 |
| Lyral FF (f) | 269 | 269 | 269 |
| Dipropylene glycol | 56 | 46 | 46 |
| Mixture of 80% (1) and 20% (2) | — | 10 | — |
| Limonene aldehyde (d) | — | — | 10 |
| Total: | 1000 | 1000 | 1000 |

What is claimed is:

1. A composition comprising from 70 to 90% by weight of 2-methylene-3-(4-methlycyclohex-3-enyl)-butanal and from 10 to 30% by weight of limonene aldehyde.

2. The composition according to claim 1, further comprising up to about 5% by weight of one or more additional olfactorily active components.

3. The composition according to claim 1, wherein the 2-methylene-3-(4-methlycyclohex-3-enyl)-butanal is present in an amount of about 80% by weight and the limonene aldehyde is present in an amount of about 20% by weight.

4. A product comprising from 0.001 to 70% by weight of a perfume composition comprising from 70 to 90% by weight of 2-methylene-3-(4-methlycyclohex-3-enyl)-butanal and from 10 to 30% by weight of limonene aldehyde.

5. The product according to claim 4, wherein the perfume composition further comprises up to about 5% by weight of one or more additional olfactorily active components.

6. The product according to claim 4, wherein the 2-methylene-3-(4-methlycyclohex-3-enyl)-butanal is present in an amount of about 80% by weight and the limonene aldehyde is present in an amount of about 20% by weight.

7. The product according to claim 4, wherein the perfume composition is present in an amount of 0.05 to 2% by weight.

8. The product according to claim 5, wherein the perfume composition is present in an amount of 0.05 to 2% by weight.

9. The product according to claim 6, wherein the perfume composition is present in an amount of 0.05 to 2% by weight.

10. A method of providing a fragrance to a composition, said method comprising:

(a) providing a composition; and (b) adding a fragrance-providing effective amount of a mixture comprising from 70 to 90% by weight of 2-methylene-3-(4-methlycyclohex-3-enyl)-butanal and from 10 to 30% by weight of limonene aldehyde.

11. The method according to claim 10, wherein the mixture further comprises up to about 5% by weight of one or more additional olfactorily active components.

12. The method according to claim 10, wherein the 2-methylene-3-(4-methlycyclohex-3-enyl)-butanal is present in an amount of about 80% by weight and the limonene aldehyde is present in an amount of about 20% by weight.

13. The method according to claim 10, wherein from 0.001 to 70% by weight of the mixture is added to the composition, based on the total combined weight of the mixture and composition.

14. The method according to claim 10, wherein from 0.05 to 2% by weight of the mixture is added to the composition, based on the total combined weight of the mixture and composition.

* * * * *